United States Patent
Forgez et al.

(10) Patent No.: US 8,586,043 B2
(45) Date of Patent: Nov. 19, 2013

(54) METHODS FOR TREATING BREAST CANCER WITH INHIBITORS OF NEUROTENSIN ACTIVATION OF NTSR1

(75) Inventors: Patricia Forgez, Paris Cedex (FR); Anne Gompel, Paris Cedex (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 86 days.

(21) Appl. No.: 13/143,259

(22) PCT Filed: Jan. 5, 2010

(86) PCT No.: PCT/EP2010/050044
§ 371 (c)(1), (2), (4) Date: Sep. 6, 2011

(87) PCT Pub. No.: WO2010/079158
PCT Pub. Date: Jul. 15, 2010

(65) Prior Publication Data
US 2011/0305633 A1    Dec. 15, 2011

(30) Foreign Application Priority Data
Jan. 7, 2009 (EP) .................................. 09305011

(51) Int. Cl.
*A61K 39/395*    (2006.01)
*C07K 16/00*    (2006.01)

(52) U.S. Cl.
USPC .................. 424/143.1; 424/130.1; 424/145.1; 530/387.1; 530/388.22

(58) Field of Classification Search
None
See application file for complete search history.

(56) References Cited

U.S. PATENT DOCUMENTS

2005/0112678 A1    5/2005    Yang

FOREIGN PATENT DOCUMENTS

| WO | 03/093828 | 11/2003 |
| WO | 2005/052194 | 6/2005 |
| WO | 2005/090603 | 9/2005 |

OTHER PUBLICATIONS

Garcia-Garayoa et al., Nuclear Med. Biol., 28(1):75-84 (2001) XP002255943.
International Search Report and Written Opinion in PCT/EP2010/050044, dated Apr. 16, 2010.
Somai et al., Biochem. Biophys Res. Commun., 295(2):482-488 (2002) XP002518144.
Souaze et al., Cancer Res., 66(12):6243-6249 (2006).

*Primary Examiner* — Christine J Saoud
*Assistant Examiner* — Jon M Lockard
(74) *Attorney, Agent, or Firm* — McAndrews, Held & Malloy Ltd.

(57) ABSTRACT

The present invention relates to methods for the treatment, the prognostic assessment and the detection of breast cancer.

1 Claim, 5 Drawing Sheets

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial
<220> FEATURE:
<223> OTHER INFORMATION: siRNA
```

```
<400> SEQUENCE: 1
aagaagttca tcagcgccat c                                            21

<210> SEQ ID NO 2
<211> LENGTH: 19
<212> TYPE: DNA
<213> ORGANISM: Artificial
<220> FEATURE:
<223> OTHER INFORMATION: siRNA

<400> SEQUENCE: 2
gcaatgttga caatatacc                                               19

<210> SEQ ID NO 3
<211> LENGTH: 15
<212> TYPE: DNA
<213> ORGANISM: Artificial
<220> FEATURE:
<223> OTHER INFORMATION: primer

<400> SEQUENCE: 3
gctgacgtag aagag                                                   15

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
cgtggagctg tacaacttca                                              20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
cagccagcag accacaaagg                                              20

<210> SEQ ID NO 6
<211> LENGTH: 18
<212> TYPE: DNA
<213> ORGANISM: Artificial
<220> FEATURE:
<223> OTHER INFORMATION: primer

<400> SEQUENCE: 6
aagcacatgt tccctctt                                                18

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
catacagctg ccgtttcaga                                              20
```

METHODS FOR TREATING BREAST CANCER WITH INHIBITORS OF NEUROTENSIN ACTIVATION OF NTSR1

The present application is filed pursuant to 35 U.S.C. 371 as a U.S. National Phase application of International Patent Application No. PCT/EP2010/050044, which was filed Jan. 5, 2010, claiming the benefit of priority to European Patent Application No. 09305011.0, which was filed on Jan. 7, 2009. The entire text of the aforementioned applications is incorporated herein by reference in its entirety.

FIELD OF THE INVENTION

The present invention relates to methods for the treatment, the prognostic assessment and the detection of breast cancer.

BACKGROUND OF THE INVENTION

Breast cancer is the most frequent cause of cancer-related deaths among women in the western world. Among these patients, one of four women dies from breast cancer, despite improvements in diagnosis, surgery, chemotherapy and the new targeted therapies. Death is associated with the metastatic development of the disease. The discovery and characterization of new contributors remain necessary in order to develop appropriate and highly specific treatments targeted to metastasis initiation and progression processes.

During 1997, more than 36 000 new cases of ductal carcinoma in situ (DCIS), representing 17% of all new breast cancers, were diagnosed in the United States. Most of these cases were diagnosed by mammography. High quality mammography is capable of finding a range of asymptomatic non-invasive lesions that cannot be palpated. These are often smaller, of lower nuclear grade, and show much subtler changes than the lesions detected with less advanced mammographic equipment in the past. Technically good mammography requires exceptional attention to detail. The need for expert radiological interpretation cannot be overemphasised. The most common mammographic finding is microcalcifications, but some lesions may present as masses or architectural distortions with or without microcalcifications. Breast Magnetic resonance imaging (MRI) has been approved by the U.S. Food and Drug Administration (FDA) since 1991 for use as a supplemental tool, in addition to mammography, to help diagnose breast cancer. MRI is useful for staging breast cancer, determining the most appropriate treatment, and for patient follow-up after breast cancer treatment. Because MRI is more sensitive than mammography, it can help detect cancer that may be missed by mammography. However, because this increased sensitivity can also lead to false positive results, which requires breast biopsy procedures, the American Cancer Society does not recommend MRI for all women.

Neurotensin (NTS) is a 13 amino acids peptide formed from a large precursor, cleaved by convertases. NTS is commonly known for its distribution along the gastrointestinal tract. Typical physiological functions for NTS include stimulation of pancreatic and biliary secretions, inhibition of small bowel and gastric motility, and facilitation of fatty acids translocation. NTS was equally reported in functions linked specifically to neoplastic progression, including proliferation of the pancreas, prostate, colon, and lung cancer cells. We have previously described a potential role of NTS in breast tumor progression (Souaze et al (2006) Cancer Res. 66:6243-6249).

NTS peripheral functions are mediated through its interaction with NTSR1 (High affinity neurotensin receptor 1). When NTSR1 is challenged with NTS, phosphatidyl inositols are hydrolyzed leading to $Ca^{2+}$ mobilization and PKC, ERK1/2, RhoGTPases, NFkappa-B, and focal adhesion kinase (FAK) activation.

Identifying patients with pathological initial stages but with a high risk of recurrence would be extremely useful, in order to individually tailor further management, in terms of more strict follow-up and/or adjuvant treatments.

SUMMARY OF THE INVENTION

The present invention relates to a method of determining the prognosis of a subject suffering from breast cancer, comprising the step of measuring the level of expression of neurotensin receptor 1 (NTSR1) in breast cancer cells obtained from said subject.

There is also provided a method for treating breast cancer, comprising the step of administering an effective amount of an inhibitor of the neurotensin activation of the neurotensin receptor 1 (NTSR1) to a subject in need thereof.

The present invention also provides a method for treating breast cancer, comprising the step of administering an effective amount of a cytotoxic agent which binds to the neurotensin receptor 1 to a subject in need thereof.

The present invention also provides a method of detecting and localizing breast cancer cells and/or metastases stemming from breast cancer cells in the body of a subject, to which a quantity sufficient for imaging of a labelled agent which binds to NTSR1 has been previously administered, comprising the step of subjecting said body to imaging.

The present invention also relates to a labelled agent which binds to NTSR1 for a diagnostic of breast cancer practised on a subject.

DETAILED DESCRIPTION OF THE INVENTION

The present invention relates to a method of determining the prognosis of a subject suffering from breast cancer, comprising the step of measuring the level of expression of NTRS1 in breast cancer cells obtained from said subject.

By "measuring the level of expression of NTRS1", it is meant measuring the percent of the breast cancer cells expressing NTRS1.

A high NTSR1 expression (such as at least 50% of percent or at least 60%, or at least 70% or at least 80% of the breast cancer cells express NTRS1) is associated with a worse prognostic, i.e. a lowest survival rate.

Typically NTSR1 expression may be measured for example by RT-PCR or immunohistochemistry performed on a sample obtained by biopsy.

In the biopsy of breast cancer, whether it is an invasive or an in situ cancer, the NTSR1 is quantitated in the cancerous cells.

The present invention also enables the evaluation of the risk of recurrence of a subject which has been surgically treated and subsequently received the appropriate treatment (such as radiotherapy, chemotherapy and/or hormonal therapy).

A method of prognosis according to the invention may be used in combination with any other methods already used for the prognostic assessment of breast cancer, including stage, demographic and anthropometric parameters, results of routine clinical or laboratory examination, including size of the tumor, histoprognostic grading, hormone receptors, oncotype, mammoprint, uPA/PAI-1 . . . .

The present invention also provides a method for treating breast cancer, comprising the step of administering an effective amount of an inhibitor of the neurotensin activation of the neurotensin receptor 1 (NTSR1) to a subject in need thereof.

Also provided is an inhibitor of the neurotensin activation of the neurotensin receptor 1 (NTSR1) for the treatment of breast cancer.

The expression "inhibitors of the neurotensin activation of NTSR1" should be understood broadly, this expression refers to agents down-regulating the expression of neurotensin or of neurotensin receptor 1, compounds that bind to neurotensin (NTS) or NTSR1 and inhibit the neurotensin activation of NTSR1, or a protease that can degrade NTS.

Examples of inhibitors of the neurotensin activation of NTSR1 may be selected from the group consisting of an agent down-regulating the expression of neurotensin or of neurotensin receptor 1, an antibody against neurotensin or a fragment thereof which binds to neurotensin, an antibody against the neurotensin receptor 1 or a fragment thereof which binds to the neurotensin receptor 1, an antagonist of the neurotensin receptor 1, and a protease that can degrade NTS.

In an embodiment of the present invention, the inhibitor of the neurotensin activation of the neurotensin receptor 1 is an agent down-regulating the expression of neurotensin or of neurotensin receptor 1 in breast cells. Typically, agent down-regulating the expression of neurotensin or of neurotensin receptor 1 comprises a nucleic acid which interferes with the expression of neurotensin or of neurotensin receptor 1.

Typically, the down-regulation of the NTS or NTRS1 expression may be measured by immunohistochemistry, binding assay, mRNA level for NTSR1 and radio-immunoassay or Enzyme link immunosorbent assay for NTS (Holtom P E, et al J Neurosci Methods. 100(1-2):151-6, 2000; Davis L G et al, J Neurosci Methods 15-23, 1985; Vincent J P Ann N Y Acad Sci., 668:90-100, 1992; Souazé F et al., J Biol Chem, 272(15):10087-94, 1997).

Examples of such agents are antisense molecules or vectors comprising said antisense molecules. Antisense molecules are complementary strands of small segments of mRNA. Methods for designing effective antisense molecules being well known (see for example U.S. Pat. No. 6,165,990), it falls within the ability of the skilled artisan to design antisense molecules able to downregulate the expression of neurotensin or of neurotensin receptor 1 in breast cells. Further examples are RNA interference (RNAi) molecules such as, for example, short interfering RNAs (siRNAs) and short hairpin RNAs (shRNAs). RNAi refers to the introduction of homologous double stranded RNA to specifically target a gene's product, in the present case neurotensin or of neurotensin receptor, resulting in a null or hypomorphic phenotype. Methods for designing effective RNAi molecules being well known (see for review Hannon and Rossi Nature. 2004 Sep. 16; 431(7006):371-8), it falls within the ability of the skilled artisan to design RNAi molecules able to downregulate the expression of neurotensin or of neurotensin receptor in breast cells.

Examples of siRNAs able to downregulate the expression of neurotensin or of neurotensin receptor in breast cells are nucleic acid molecules which comprise one of the following sequences:

```
siRNA NTSR1:
5'-AAGAAGTTCATCAGCGCCATC-3'    (SEQ ID NO: 1)

siRNA NTS:
5'-GCAATGTTGACAATATACC-3'      (SEQ ID NO: 2)
```

In a further embodiment of the invention, the inhibitor of the neurotensin activation of the neurotensin receptor 1 is an antibody against neurotensin or a fragment thereof which binds to neurotensin, an antibody against the neurotensin receptor 1 or a fragment thereof which binds to the neurotensin receptor 1.

The person skilled in the art will be aware of standard methods for production of such specific antibody or fragment thereof. For example, specific antibodies or fragment thereof may be generated by immunizing an animal with neurotensin or with NTSR1 and by selecting the antibodies which inhibit the neurotensin activation of the neurotensin receptor 1.

Typically the inhibition of the neurotensin activation of the neurotensin receptor 1 may be measured with biological assays estimating the second messenger level, or the oncogenic cellular effect, or the morphological changes of the cells (Skrzydelski D et al Mol Pharmacol. 64(2):421-9 2003; Xu-van Opstal W Y et al, Microsc Res Tech. 28(5):440-7 1994; Souaze F et al. Can Res 66(12):6243-9 2006).

The person skilled in the art will be aware of standard methods for production of both polyclonal and monoclonal antibodies and fragments thereof which binds to NTS or to NTSR1. Antibody fragments, particularly Fab fragments and other fragments which retain epitope-binding capacity and specificity are also well known, as are chimeric antibodies, and "humanized" antibodies, in which structural (not determining specificity for antigen) regions of the antibody are replaced with analogous or similar regions from another species. Thus antibodies generated in mice can be "humanized" to reduce negative effects which may occur upon administration to human subjects. Chimeric antibodies are now accepted therapeutic modalities with several now on the market. The present invention therefore comprehends use of antibody specific for neurotensin or NTSR1 which include $F(ab')_2$, $F(ab)_2$, Fab, Fv and Fd antibody fragments, chimeric antibodies in which one or more regions have been replaced by homologous human or non-human portions. The person skilled in the art will also be aware that fragments such as for example ScFv fragments and divalent ScFv-type molecules can be prepared using recombinant methods.

In a further embodiment of the present invention, the inhibitor of the neurotensin activation of the neurotensin receptor 1 is an antagonist of the neurotensin receptor 1. Antagonists of the neurotensin receptor 1 are well known. SR48692 SR14294A are commonly used inhibitors of NTSR1 (see for example Gully et al. 1993, Proc. Natl. Acad. Sci. 90, 65-69 and Gully et al. 1997, J. Pharmacol. Exp. Ther. 280, 802-812). WO96/32382, WO95/32218, U.S. Pat. No. 5,430,047, U.S. Pat. No. 5,668,279 and EP0699438, for example, disclose families of antagonists of the neurotensin receptor 1.

In a further embodiment of the invention, the inhibitor of the neurotensin activation of the neurotensin receptor 1 is a protease that can degrade NTS. Examples of proteases that can degrade NTS are mast Cell carboxypeptidase A, neurolysin or human skin chymase. The protease may be administered to the subject in need thereof in its proteineous form or by gene therapy, for example by using a vector which enables the expression of the protease in situ.

The expression of NTSR1 by breast cancer cells enables the specific targeting of breast cancer cells with cytotoxic agent which binds to the neurotensin receptor 1.

The present invention provides a method for treating breast cancer, comprising the step of administering an effective amount of a cytotoxic agent which binds to the neurotensin receptor 1 to a subject in need thereof.

Also provided is a cytotoxic agent which binds to the neurotensin receptor 1 for the treatment of breast cancer.

Examples of cytotoxic agents which bind to the neurotensin receptor 1 may be selected from the group consisting of an antibody against the neurotensin receptor 1 or a fragment thereof which binds to the neurotensin receptor 1, neurotensin or a neurotensin analogue conjugated with a cytotoxic drug, and neurotensin or a neurotensin analogue labelled with a cytotoxic radioisotope. The cytotoxic agent which binds to the neurotensin receptor 1 may also be an antimetabolite.

Typically said antibody against the neurotensin receptor 1 or said fragment thereof which binds to the neurotensin receptor 1, may be conjugated with a cytotoxic drug or labelled with a cytotoxic radioisotope.

Alternatively, said antibody against the neurotensin receptor 1 or said fragment thereof which binds to the neurotensin receptor may trigger antigen-dependent cell-mediated cytotoxicity (ADCC) and/or complement dependent cytotoxicity (CDC). This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. J Exp Med. 1992 Oct. 1; 176(4):1191-5 and Shopes B. J Immunol. 1992 May 1; 148(9):2918-22.).

Neurotensin analogues are well known, WO98/33531, WO00/78796, WO2007/093373, U.S. Pat. No. 6,312,661 and U.S. Pat. No. 5,760,188, for example, provide families of neurotensin analogues. The neurotensin analogue may be an antagonist or an agonist of NTSR1.

Examples of cytotoxic drugs are platinum salts, taxanes, vinca derivatives and analogues, gemcitabine, methotrexate, doxorubicin, cytotoxin such as *Pseudomonas* exotoxin, g protein, and g protein coupled receptor inhibitors.

Common cytotoxic radioisotopes are, for example, $^{131}$I, $^{90}$Y, $^{77}$Lu, $^{67}$Cu, $^{186}$Re, $^{188}$Re, $^{212}$Bi and $^{213}$Bi.

In the context of the invention, the term "treating" or "treatment", as used herein, means reversing, alleviating, inhibiting the progress of, or preventing the disorder or condition to which such term applies, or reversing, alleviating, inhibiting the progress of, or preventing one or more symptoms of breast cancer.

By a "therapeutically effective amount" of an inhibitor of the neurotensin activation of the neurotensin receptor 1 or of a cytotoxic agent which binds to the neurotensin receptor 1 is meant a sufficient amount to treat breast cancer, at a reasonable benefit/risk ratio applicable to any medical treatment. It will be understood, however, that the total daily usage of the inhibitor or of the cytotoxic agent will be decided by the attending physician within the scope of sound medical judgment. The specific therapeutically effective dose level for any particular subject in need thereof will depend upon a variety of factors including the stage of breast cancer being treated and the activity of the specific inhibitor/cytotoxic agent employed, the age, body weight, general health, sex and diet of the subject, the time of administration, route of administration, the duration of the treatment; drugs used in combination or coincidental with the and like factors well known in the medical arts. For example, it is well known within the skill of the art to start doses of the compound at levels lower than those required to achieve the desired therapeutic effect and to gradually increase the dosage until the desired effect is achieved.

Typically medicaments according to the invention comprise an inhibitor of the neurotensin activation of the neurotensin receptor 1 or a cytotoxic agent which binds to the neurotensin receptor 1, together with a pharmaceutically-acceptable carrier. A person skilled in the art will be aware of suitable carriers. Suitable formulations for administration by any desired route may be prepared by standard methods, for example by reference to well-known text such as Remington; The Science and Practice of Pharmacy.

A method of treatment according to the invention may be used in combination with any other therapeutic strategy for treating breast cancer, e.g. surgery, external radiotherapy, chemotherapy (such as treatment with doxorubicin, epirubicin, cyclophosphamide, docetaxel, paclitaxel, capecitabine, ixabepilone, methotrexate or fluorouracil) or hormonal therapy, or targeted therapies (such as HER2-targeted therapies with for example trastuzumab or lapatinib or other targeted therapies such as inhibition of growth factors pathways, like for example treatment with bevacizumab) or cytokine therapy.

In a particular embodiment of the invention, if breast cancer cells are positive for hormone receptors (estrogen and/or progesterone receptors), a treatment according to the invention is used in combination with hormonal therapy, also called anti-estrogen therapy.

Examples of hormonal therapy are:

Treatment with Selective estrogen-receptor response modulators (SERMs): The best-known SERM is tamoxifen. Other examples of SERMs are: raloxifene and toremifene. Tamoxifen is usually recommended for women who have not yet gone through menopause, although it can be used after menopause as well.

Treatment with Aromatase inhibitors: These medications, which include treatments with anastrozole, exemestane or letrozole, reduce the amount of estrogen produced in a woman's body after she goes through menopause.

Treatment with Estrogen-receptor downregulators (ERDs): ERDs destroy the estrogen receptors in the cells, which prevents the estrogen from getting its message through. fulvestrant is an ERD approved for use in postmenopausal women with advanced breast cancer.

Ovarian shutdown or removal (oophorectomy). The ovaries are the main source of estrogen in women before menopause. Shutting the ovaries down temporarily (for a set period of time) or even permanently can reduce the amount of estrogen in the body. Treatments include medicines such as goserelin or leuprolide, given by injection once a month for several months to stop the ovaries from producing estrogen.

Typically, before applying a method of treatment according to the present invention to a subject suffering from breast cancer, a diagnostic test may be performed in order to determine whether the breast cancer displays NTSR1-expressing cells. By performing such a pre-treatment diagnostic test, it is possible to determine whether a subject would be responsive to a method of treatment according to the invention.

It falls within the ability of the skilled artisan to carry out such a diagnostic test. Typically NTSR1 expression may be measured for example by RT-PCR or immunohistochemistry performed on a sample obtained by biopsy.

Alternatively, levels of neurotensin or a precursor thereof such as proneurotensin in a sample obtained from the subjects may be determined in order to treat only those subjects having an elevated level of neurotensin or a precursor thereof such as proneurotensin. Examples of samples obtained from the subjects are whole blood sample, plasma sample or serum sample, obtained for example from samples collected from peritumoral veins. Neurotensin or proneurotensin survey may also be used to detect an eventual recurrence of the tumor and/or of metastases. Examples of method for measuring the levels of proneurotensin are given in WO2006/079528, in Ernst et al., Peptides 27 (2006) 1787-1793 and in Friry et al, Biochemical and Biophysical research Communication 290, 1161-1168 (2002).

In an embodiment of the invention, the subject in need thereof is a subject with an early stage, such as stage 0 or I, breast cancer displaying NTSR1-expressing cells.

In a further embodiment of the invention, the subject in need thereof is a subject with an advanced stage, such as stage III or IV, breast cancer displaying NTSR1-expressing cells.

The stages of breast cancer are defined for example in UICC. TNM Classification of Malignant Tumours. 6th ed. Sobin L H, Wittekind Ch (eds) Wiley-Liss: New York, 2002.

The present invention also provides a method of detecting and localizing breast cancer cells and/or metastases stemming from breast cancer cells in the body of a subject, to which a quantity sufficient for imaging of a labelled agent which binds to NTSR1 has been previously administered, comprising the step of subjecting said body to imaging.

The present invention also relates to a labelled agent which binds to NTSR1 for a diagnostic of breast cancer practised on a subject.

In a particular embodiment of the invention, the invention enables the diagnostic of breast cancer at a very early stage of the disease such as at stage 0.

Typically the present invention provides a method of detecting and localizing ductal carcinoma in situ.

Examples of labelled agents which bind to NTSR1 may be selected from the group consisting of a labelled antibody against the neurotensin receptor 1 or a fragment thereof which binds to the neurotensin receptor 1, a labelled neurotensin or a labelled neurotensin analogue. Typically the label may be a fluorophore, a radioactive isotope or a paramagnetic agent such as Gadolinium.

Labelled neurotensin analogue and their uses for imaging are well known see for example: Garcia-Garayoa et al. Eur J Nucl Med Mol Imaging. 2009 January; 36(1):37-47; Janssen et al. Cancer Biother Radiopharm. 2007 June; 22(3):374-81; Maina et al., Eur J Nucl Med Mol Imaging. 2007 November; 34(11):1804-14; Nock et al., J Med Chem. 2006 Jul. 27; 49(15):4767-76; Zhang et al., Nucl Med Biol. 2006 May; 33(4):505-12; García-Garayoa et al., Nucl Med Biol. 2006 May; 33(4):495-503; Bläuenstein P et al., Cancer Biother Radiopharm. 2004 April; 19(2):181-8; Buchegger et al., J Nucl Med. 2003 October; 44(10):1649-54; Achilefu et al., J Med Chem. 2003 Jul. 17; 46(15):3403-11; de Visser et al., Eur J Nucl Med Mol Imaging. 2003 August; 30(8):1134-9; Hillairet De Boisferon et al., Bioconjug Chem. 2002 May-June; 13(3):654-62; Bruehlmeier et al., Nucl Med Biol. 2002 April; 29(3):321-7; WO98/33531; WO00/78796; WO2007/093373; U.S. Pat. No. 6,312,661 and U.S. Pat. No. 5,760,188.

Depending on the label used, different imaging techniques may be used such as a chest x-ray, mammograms, bone scans, computed tomography (CT) scans, magnetic resonance imaging (MRI), positron emission tomography (PET) scans, or PET/CT.

In the following, the invention will be illustrated by means of the following example as well as the tables and figures.

FIGURE LEGENDS

A) Left, one μg of total RNA from HBEC or whole gland were reverse-transcribed and a PCR experiment specific for NTS was performed. Right, one μg of total RNA from HBEC cells (control, treated with 10 nM estradiol (E2) with or without 1 μM ICI 182780) was reverse-transcribed. A PCR experiment was performed using specific primers for NTS and GAPDH.

B) Normal duct exposed to NTS antibody at 1/500 dilution (1), after pre-incubation with the antigen peptide for 2 h at 10 nM (2), or without primary antibody (3), and lobule exposed to NTS antibody (4). Normal tissue exposed to NTS antibody at 1/500 dilution adjacent to tumor duct (5), lobule (6). The original magnification was 200×.

A) NTS immunohistochemistry was performed on IDCs, ductal (1) and invasive (2) components, magnification 200× for (1) and 400× for (2). B) NTS and NTSR1 transcripts in IDCs. One μg of total RNA from 11 patients with IDCs were reverse-transcribed, and specific PCR was performed for NTS, NTSR1 receptor, or GAPDH (control). The SBR grade is indicated below each line. C) Example of NTS and NTSR1 regional co-localization by immunohistochemistry for NTS (right) and NTSR1 (left) at the original magnification 400×.

Kaplan-Maier analysis for global survival duration in both groups with low (<80%) and high (≥80%) NTSR1 expression. Probability of overall death for patients with high NTSR1 expression (n=38) versus patients with low NTSR1 expression (n=68).

A) Transcript analysis for NTS, NTSR1, ER-alpha, and PR for over-expressing clones, NTS-h with high NTS expression, and NTS-1 with low NTS expression, are compared to wild type cells, MCF-7.

B) Cell proliferation rate for MCF-7 and NTS-h. The percentage of cells for each time point was compared to the number of cells originally seeded.

B) Image from a mouse bearing a small tumor. Photograph (1), planar image at 60 min (2), 5 h (3), and 24 h (4) post injection. The arrow shows the tumor. Kidneys were indicated by K, and the bladder was indicated by B.

Acquisition periods were from 0 to 60 min for the time point at 1 h, and 45 min for the three points at 5, 24 and 30 h.

Tables

TABLE 1

| Patients clinical characteristics | |
|---|---|
| | IDCs n = 106 |
| Age in years [mean ± SD] | 57.96 ± 14.04 |
| Menopausal status | |
| Post menopausal patients [n (% of patients)] | 69 (65%) |
| Age at menopause [mean ± SD] | 50.96 ± 3.05 |
| Family history of breast cancer [n/number of cases studied (% of patients)] | 18/79 (23%) |

TABLE 1-continued

Patients clinical characteristics

| | IDCs n = 106 |
|---|---|
| HRT use [n/number of cases studied (% of patients)] | 17/92 (18%) |
| Follow-up in months [mean ± SD] | 67.9 ± 41.93 |
| Positive estrogen receptor [n/number of cases studied (% of patients)] | 69/100 (69%) |
| Positive progesterone receptor [n/number of cases studied (% of patients)] | 71/99 (71.7%) |
| Tumor size (cm) [mean ± SD] | 2.3 ± 1.43 |
| SBR grade [n] | |
| 1 | 33 |
| 2 | 49 |
| 3 | 24 |
| Number of patients N+ [n/number of cases studied (% of patients)] | 42/104 (40.4%) |
| Number of invaded nodes [mean ± SD] | 1.32 ± 2.55 |
| Recurrence during follow-up [n (% of patients)] | 26 (25%) |
| Deaths during follow-up [n (% of patients)] | 11 (10.4%) |
| Adjuvant therapy (number of cases studied) | 102 |
| Radiotherapy [n (% of patients)] | 96 (94%) |
| Chemotherapy [n (% of patients)] | 36 (35.5%) |
| Tamoxifen use [n (% of patients)] | 78 (76.4%) |

SBR; Scarff Bloom and Richardson,
n = number of patients,
SD = standard deviation

TABLE 3

Prognosis factors and deaths stratified by NTSR1 expression in the invasive component of IDCs.

| | NTSR1 n = 106 | | |
|---|---|---|---|
| | <80% n = 68 | >80% n = 38 | P |
| Positive estrogen receptor [n/number of cases studied] | 46/64 | 23/36 | NS |
| Positive progesterone receptor [n/number of cases studied] | 46/63 | 25/36 | NS |
| Tumor size (cm) | | | |
| [number of cases studied] | 68 | 38 | |
| [mean (SD)] | 2.08 ± 1.35 | 2.71 ± 1.4 | 0.007 |
| SBR grade [number of cases studied] | 68 | 38 | |
| 1 | 26 | 7 | |
| 2 | 31 | 18 | |
| 3 | 11 | 13 | 0.036 |
| Number of invaded nodes [number of cases studied] | 66 | 38 | |
| [mean ± SD] | 0.86 ± 1.7 | 2.11 ± 3.4 | 0.05 |
| Recurrence during follow-up [n/number of cases studied] | 13/67 | 13/38 | 0.09 |
| Deaths during follow-up [n/number of cases studied] | 2/68 | 9/38 | 0.0025 |
| Adjuvant therapy (102 cases studied) | 65 | 37 | |
| Radiotherapy [n] | 61 | 35 | NS |

TABLE 2

Prognosis factors and deaths stratified by NTS expression in the ductal and invasive components of IDCs.

| | NTS Ductal component n = 87 | | | NTS Invasive component n = 103 | | |
|---|---|---|---|---|---|---|
| | NO n = 31 | YES n = 56 | P | NO n = 55 | YES n = 48 | P |
| Positive estrogen receptor [n/number of cases studied (SD)] | | | | 30/49 | 36/47 | NS |
| Positive progesterone receptor [n/number of cases studied (SD)] | | | | 32/51 | 37/45 | 0.034 |
| Tumor size (cm) | | | | | | |
| [number of cases studied] | 30 | 52 | | 54 | 44 | |
| [mean ± SD] | 2.36 ± 1.7 | 2.22 ± 1.25 | NS | 2.43 ± 1.7 | 2.03 ± 0.9 | NS |
| SBR grade [number of cases studied] | 31 | 56 | | 52 | 47 | |
| 1 | 7 | 21 | | 16 | 17 | |
| 2 | 13 | 26 | | 25 | 22 | |
| 3 | 11 | 9 | NS | 14 | 9 | NS |
| Number of Invaded nodes | | | | | | |
| [number of cases studied] | 30 | 54 | | 52 | 48 | |
| [mean ± SD] | 1.17 ± 2.3 | 1.66 ± 3 | NS | 1.23 ± 2 | 1.49 ± 3 | NS |
| Recurrence during follow-up [n/n of patient studied] | 6/31 | 14/56 | NS | 15/55 | 11/47 | NS |
| Deaths during follow-up [n/n of patients studied] | 2/31 | 7/56 | NS | 5/55 | 6/48 | NS |
| Adjuvant therapy | 30 | 53 | | 51 | 47 | |
| Radiotherapy [n] | 29 | 50 | NS | 48 | 46 | NS |
| Chemotherapy [n] | 12 | 19 | NS | 19 | 16 | NS |
| Tamoxifen use [n] | 25 | 38 | NS | 41 | 34 | NS |

TABLE 3-continued

Prognosis factors and deaths stratified by NTSR1 expression in the invasive component of IDCs.

| | NTSR1 n = 106 | | |
|---|---|---|---|
| | <80% n = 68 | >80% n = 38 | P |
| Chemotherapy [n] | 17 | 19 | 0.01 |
| Tamoxifen use [n] | 49 | 29 | NS |
| NTS [n/number of cases studied] | 28/65 | 20/37 | NS |

TABLE 4

Correlation of the subpopulation co-expressing NTS and NTSR1 with the major prognosis factors.

| | NTS invasive component n = 48 | | |
|---|---|---|---|
| | NTSR1 <80% n = 28 | NTSR1 >80% n = 20 | P |
| Positive estrogen receptor [n/number of cases studied] | 24/27 | 12/20 | 0.049 |
| Tumor size (cm) | | | |
| [number of cases studied] | 28 | 20 | |
| [mean ± SD] | 2.08 ± 1.15 | 2.37 ± 1.16 | |
| SBR grade [number of cases studied] | 28 | 20 | |
| 1 | 14 | 3 | |
| 2 | 12 | 10 | |
| 3 | 2 | 7 | 0.011 |

EXAMPLE

In the following description, all molecular biology experiments for which no detailed protocol is given are performed according to standard protocol.

Abbreviations

NTS, Neurotensin; NTSR1, High affinity neurotensin receptor 1; IDCs, Invasive Ductal Carcinomas; SBR grade, Scarff-Bloom-Richardson grade, ER, estrogen receptor, PR, progesterone receptor, HBEC, human breast epithelial cells.

Summary

We investigated the expression of NTS and NTSR1 in normal human breast tissue and in invasive ductal breast carcinomas (IDCs) by immunohistochemistry and RT-PCR. NTS is expressed and up-regulated by estrogen in normal epithelial breast cells. NTS is also found expressed in the ductal and invasive components of IDCs. The high expression of NTSR1 is associated with the SBR grade, the size of the tumor, and the number of metastatic lymph nodes. Furthermore, the NTSR1 high expression is an independent factor of prognosis.

Results

NTS Expression in Normal Epithelial Breast Cells is Regulated by Estradiol.

Figure 1:
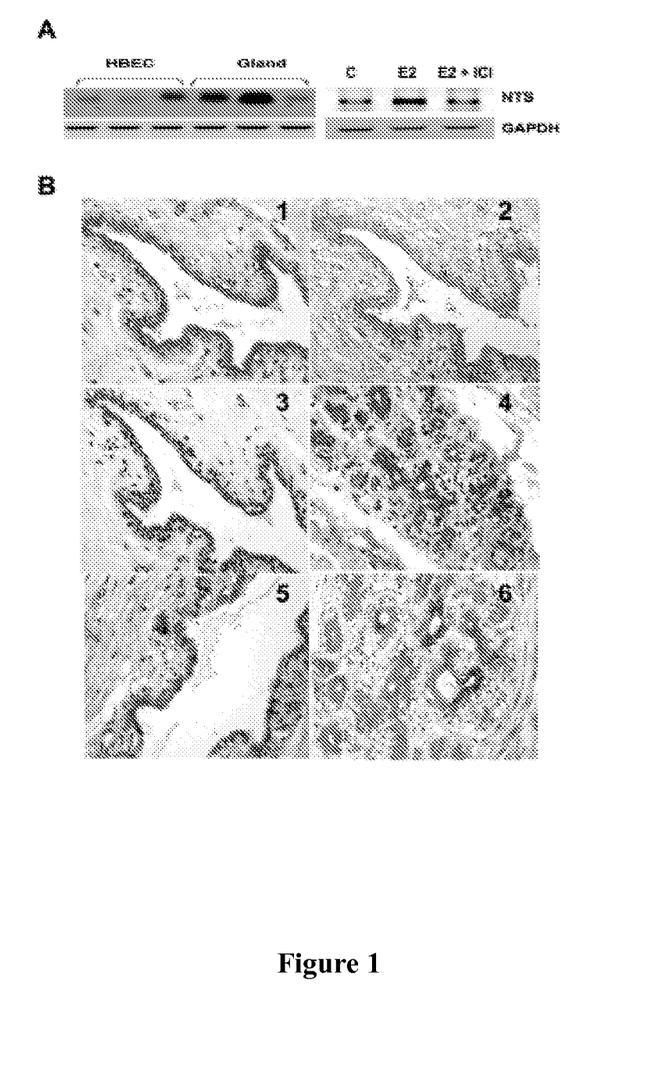
FIG. 1: Neurotensin expression in normal breast tissue.

We hypothesized that NTS is also expressed in normal human breast tissue, and studied NTS transcript on normal mammary glands, and on eight different human breast epithelial cells (HBEC) cultures. We consistently detected NTS amplicon with low to medium intensity. Typical examples are shown in FIG. 1A left. In order to evaluate if NTS gene is also regulated by estradiol in human breast, HBEC were exposed to estradiol. As shown in FIG. 1A right, an enhancement of NTS transcripts was observed. This effect was abolished when ICI 182780, a pure anti-estrogen, was added concomitantly to estradiol (FIG. 1A right) suggesting that estrogen receptors participate in the NTS gene regulation in human breast tissue. Corroborating these results, NTS expression was positively detected by immunohistochemistry in 19 (76%) biopsies of normal breast tissues from 25 premenopausal women. We observed NTS labeling within sparse epithelial cells of ducts and lobules (FIGS. 1B, 1 and 4). On the same slide we noticed that the lobular structures were labeled with a more intense staining than the duct structures. We also noticed that the normal adjacent tissue of invasive ductal breast carcinomas (IDCs) was very often labeled by NTS antibody, with similar intensity and cellular distribution as in the tissue from healthy women (FIGS. 1B, 5 and 6).

NTS Expression in Invasive Ductal Breast Carcinomas

Figure 2:
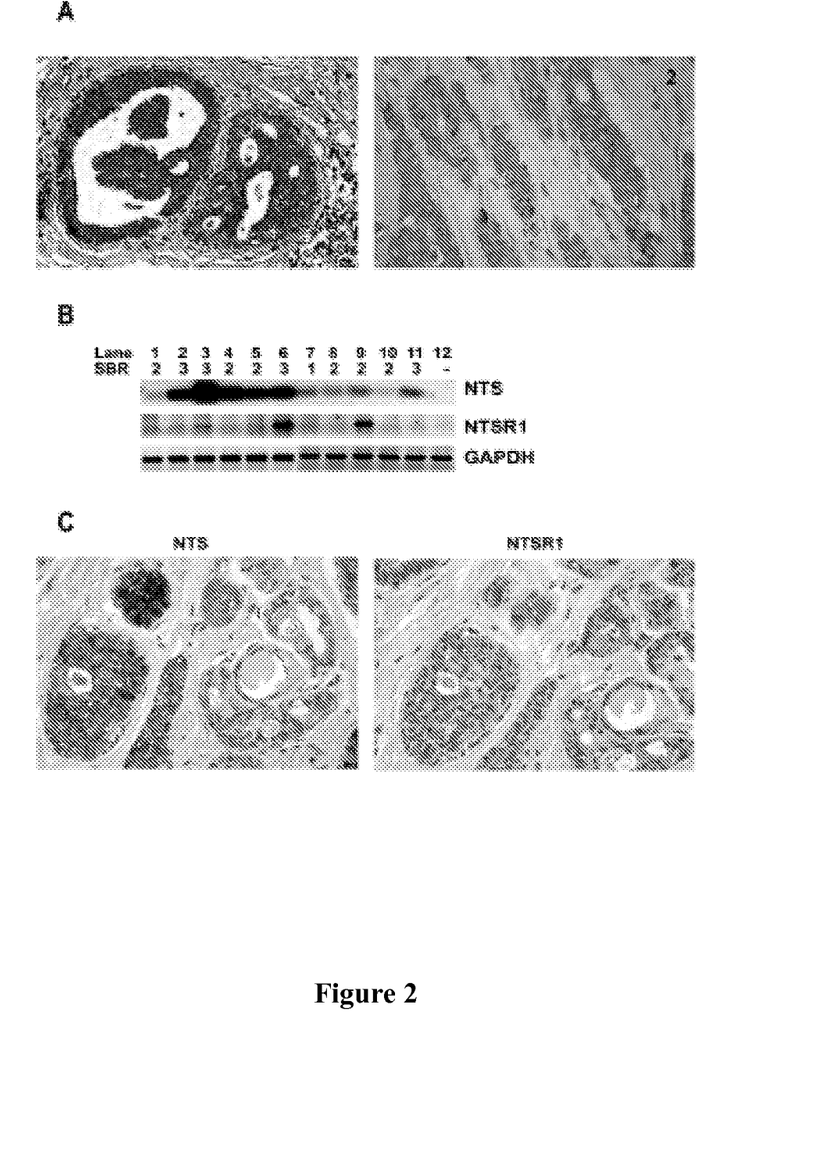
FIG. 2: Neurotensin expression in IDCs

In order to evaluate the status of NTS and NTSR1 in breast cancer we studied their respective expression in 106 IDCs. Details of clinical data, pathological characteristics, and treatment modulations are shown in table 1. NTS was graded in the invasive and ductal components in the patients' IDCs. In most cases, a large amount of cells were positively labeled with NTS antibody (FIG. 2A). NTS positive labeling in invasive component is significantly correlated with the positive labeling in the ductal component (P=0.004). In both cases, NTS labeling was cytosolic (FIG. 2A). Using RT-PCR, we confirmed the high expression of NTS transcript in 9 of 11 breast cancer tissues (FIG. 2B). Five patients exhibited a very strong expression of NTS transcript (FIG. 2B, lane 2-6) and four others displayed a weaker expression (FIG. 2B, lane 7-9 and 11). No correlation was observed with prognosis factors and disease progression (tumor size, grade, number of invaded nodes, recurrence, and death) with NTS expression, neither in the ductal nor in the invasive components (Table 2). The only correlation found, was between PR and NTS expression in the invasive component. NTS is neither a marker nor associated with tumor progression in breast cancer.

NTSR1 Expression in IDCs

NTSR1 staining in IDCs showed that NTSR1 expression was spread throughout many tumor cells in the invasive and ductal components. The labeling was granular and mostly cytosolic. In the invasive component of studied IDCs, the majority exhibited a high proportion of NTSR1 positive cells (from 50 to 100%). We hypothesized that the deleterious effects of NTS should occur in tumors containing a very high proportion of NTSR1 expressing cells. We focused on the 35% of patients in which 80% or more of the tumor cells expressed NTSR1. Expression of NTSR1 was verified by RT-PCR on frozen tissues from 11 patients. As shown in FIG. 2B, three patients expressed NTSR1 (lane 3, 6, 9) with two showing a very high amplicon amount (FIG. 2B lane 6, 9).

Figure 3:
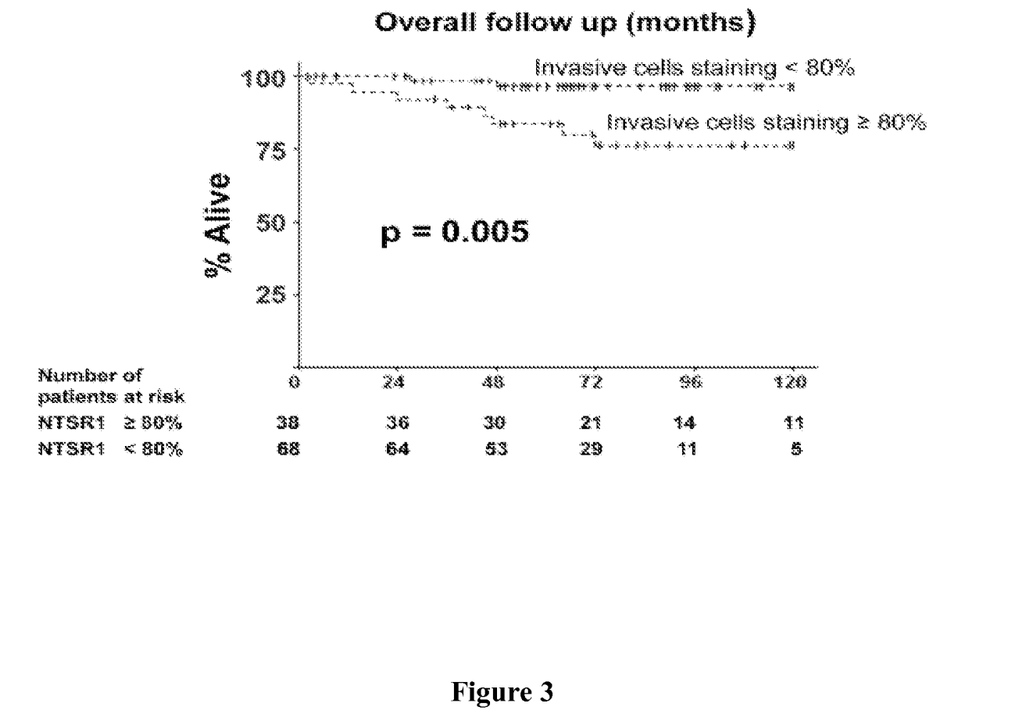
FIG. 3: NTSR1 expression in IDCs and global survival duration

The characteristics of the women exhibiting high NTSR1 expression (≥80% of tumor cells) are shown in table 3. High NTSR1 expression was associated with a larger tumor size (p<0.01), SBR grade 3 (p<0.05), the number of positive lymph nodes (p<0.05), and as a consequence it was also associated with chemotherapy (p<0.01). Using univariate analysis we found that patients with high expression of NTSR1 had a significantly worse prognosis than those with low NTSR1 expression (ten years survival rate of 66.2% versus 96.5%; p=0.01). Kaplan-Meier survival graph up-to 10 years, and number of patients at risk during this period of time are shown in FIG. 3. Multivariate analysis with a Cox model adjusted for major prognosis risk factors, age, tumor size, SBR grade, positive ER status and lymph nodes, showed that high NTSR1 expression remained an independent prognosis marker. The relative risk of dying in women with expression of NTSR1≥80% compared to women with expression of NTSR1<80% was significantly increased (RR=5.29, 95% confidence interval [1.04-26.88], p=0.044).

NTSR1 Paracrine Regulation

Within the 48 patients expressing NTS in the invasive component, 20 (42%) exhibited high expression of NTSR1 (≥80%), corresponding to 20% of the whole population. Examining adjacent tissue sections of these patients, a clear regional co-localization of the ligand and its receptor was detected in all IDCs (FIG. 2C). Within the population co-expressing NTS and NTSR1 the distribution among the SBR grades was altered as compared to the total population, with few patients in the grade 1 and most patients in the grade 3 (p<0.05). The size of the tumor, the recurrence and the number of deaths were higher in this subpopulation than in the total population. In addition, the ER alpha positivity, characterized as a differentiated and good prognosis marker, was correlated with the NTS and low NTSR1 expression (p<0.05) (Table 4).

MCF-7 Expressing NTS

Figure 4:
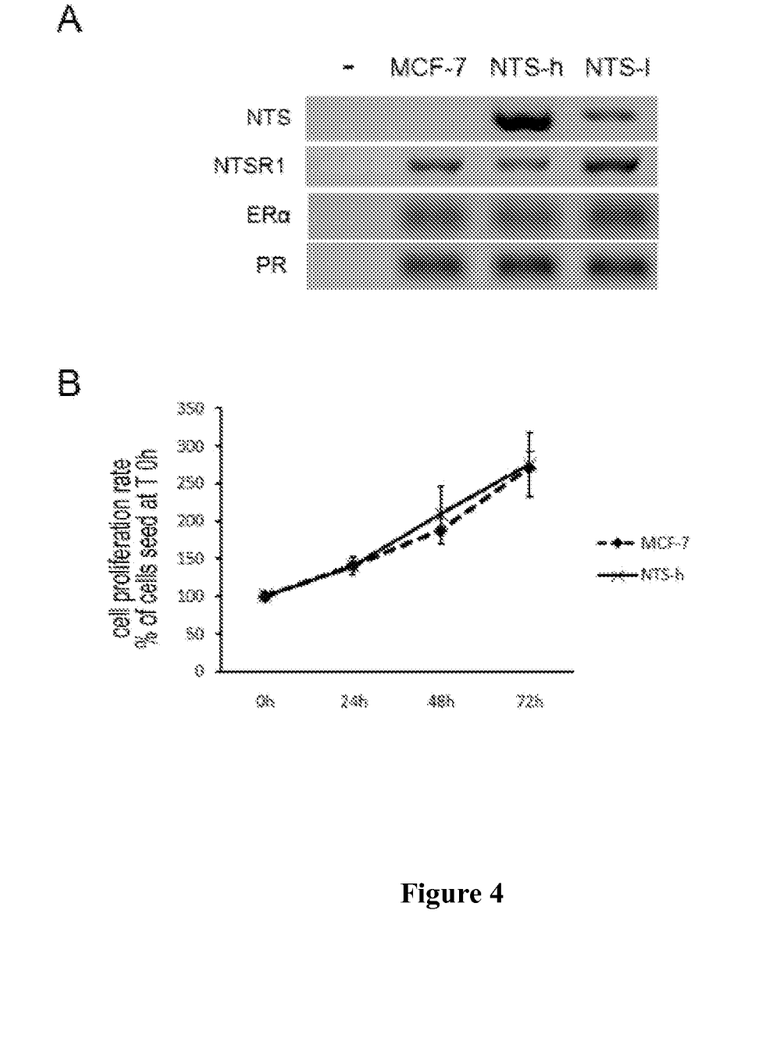
FIG. 4: Characterization of MCF-7 clones over-expressing NTS

In order to assess the role of NTS in breast cancer progression, hormone dependent breast cancer cells, MCF-7, were stably transfected with NTS coding sequence. Two clones were selected with differential expression of NTS based on the amount of NTS transcript, NTS-h with high expression of NTS, NTS-1 with low expression of NTS (FIG. 4A). Expression of NTS did not change the expression of the steroid receptors, ER alpha and PR (FIG. 4A). The NTS expressing clones were still responsive to hormonal treatment estradiol and progesterone (data not shown). As shown in FIG. 4 B, no difference in cell proliferation rate was detected between wild type cells and NTS-h. Nevertheless, when MCF-7 and NTS-h cells were xenografted into nude mice, only NTS-h cells induced tumors.

Tumor Detection

Figure 5:
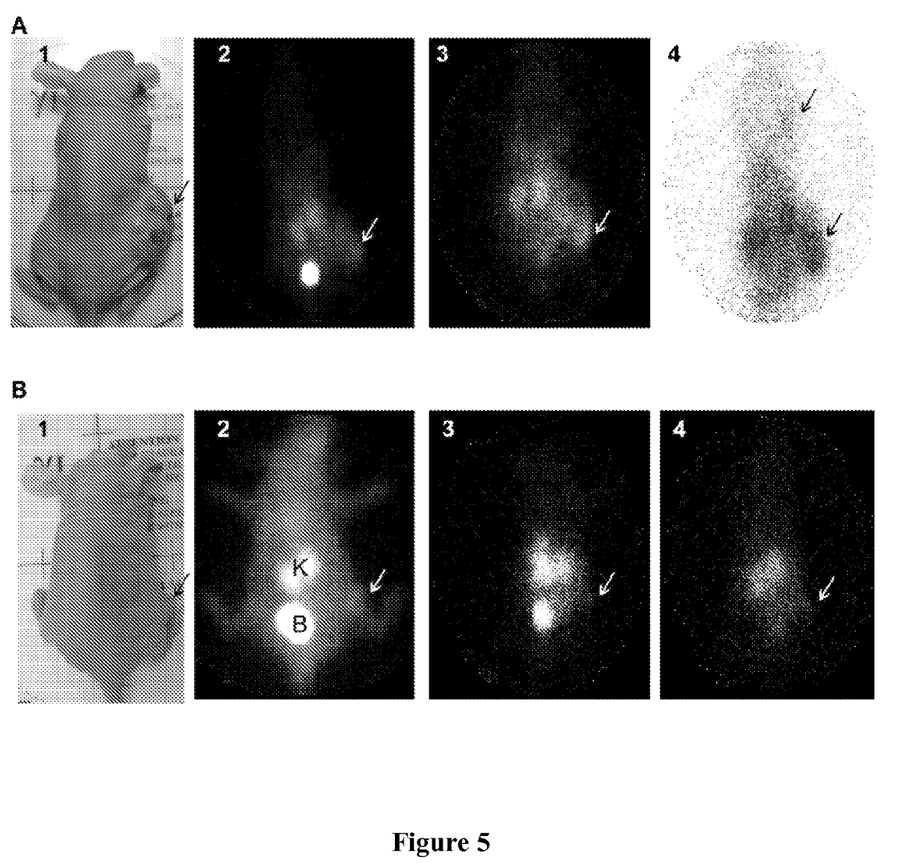
FIG. 5: Planar images of female nude mice grafted with NTS-h cells. Injected with a DTPA($^{111}$In)-NTS-analogue A) Image from a mouse bearing a large tumor. Photograph (1), planar scintigraphy image at 5 h (2) and 24 h (3) and 30 h post injection (4). In 1, 2, 3, and 4 the lower arrow shows the tumor, in 4 the upper arrow show an axillary lymph node metastasis observed after the animal dissection.

In order to demonstrate the possible tumor detection using NTSR1 expression in mammary cells, planar scintigraphy imaging was performed with a DTPA($^{111}$In)-NTS-analogue on two mice. A mouse bearing a large tumor, (FIG. 5 A) and a mouse bearing a small tumor, 2100 mg and 146 mg, respectively were tested. The accumulation of DTPA($^{111}$In)-NTS-analogue was clearly observed in tumors on planar images acquired at early and late times: 1, 5 and 24 h post-injection. Kidneys and bladder were the only sites where radioactivity accumulated in normal organs, seen mainly at 1 and 5 h post-injection. Notably, scintigraphy imaging performed after 30 h post-injection on the mice bearing a large tumor showed radioactivity accumulation in the axillary homo-lateral lymph nodes area (see FIG. 5 A panel 4 upper arrow). After animal dissection, two metastatic axillary lymph nodes of 187 and 90 mg respectively, were detected. The contro-lateral lymph node weight was 30 mg.

Conclusions

We evaluated the status of NTSR1 as a contributor in human breast cancer progression. One approach to address this question is to determine if paracrine NTS regulation is associated with the patients' poor outcome. We suspected that the contribution of NTSR1 in tumorigenesis occurred from local and sustained activation of the receptor rather than from circulating NTS, because NTS is a highly degradable peptide and its blood concentration rapidly drops after its release. It has been demonstrated that sustained activation of NTSR1 results in persistent NTSR1 recycling as well as signalization activation, including ERK1/2 (Toy-Miou-Leong et al. (2004) J. Biol. Chem. 279:12636-12646), and causes sustained gene activation of MMP9 and Bcl-2 (Souaze et al (2006) Cancer Res. 66:6243-6249). In human tumor, these conditions would be satisfied if NTS is synthesized and released within the vicinity of NTSR1 expressing cells. NTSR1 expression is an early event of cell transformation, because of the resulting NTSR1 promoter activation by the Wnt/β-catenin pathway (Souaze et al. (2006) carcinogenesis 27:708-716). Here we showed that NTSR1 is highly expressed (≥80%) in 35% of the patients with a granular labeling mostly cytosolic suggesting an intense receptor endocytosis.

We observed the expression of NTS and NTS mRNA in HBEC and demonstrated that NTS is an estrogen target gene in those cells. We also observed expression of NTS in tumor cells of the ductal and invasive components in breast IDCs, with a strong statistical correlation of NTS expression in both components. This latter finding, with a similar NTS repartition within the low or high NTSR1 expressing patients, indicates that NTS gene remains constitutively expressed during the neoplastic process, rather than being deregulated. In parallel, we observed a frequent regional co-localization of both markers in adjacent tissue sections from the same tumor, suggesting NTSR1 activation. Together with the expression of NTSR1, these data validate our hypothesis of the NTS paracrine regulation of transformed epithelial cells during the neoplastic process, with NTS released from the surrounding normal breast tissue or from the breast tumor.

High NTSR1 expression was significantly associated with the SBR grade, the size of the tumor, and the number of metastatic lymph nodes, and ultimately with death of the patients. These findings point out that the poor prognosis attributed to patients with highly NTSR1 expressing IDCs may be directly related to the expression of its natural ligand NTS, with the continuous activation of NTSR1, leading to enhanced cancer cell survival, invasiveness potential, and metastasis.

Experiments using ectopically expressing NTS cells confirm this hypothesis. As the expression of steroid receptors was not affected by NTS in these cell lines, only cells highly expressing NTS were able to develop tumors when xenografted in mice without estradiol supplementation. Tumor growth is absent in wild type MCF-7 cells in these conditions whereas in NTS expressing cells, tumors were observed with a slow process (≥6 months). Tumor formation was also observed in MCF-7 cells expressing NTS, when cells were injected in the mammary gland and the mice treated daily with estradiol. Under these conditions, tumor growth is a faster process showing 350 mg tumors after 2 months of growth (data not shown).

In addition, we were able to demonstrate the benefice of using a labeled NTS-analogue for the detection of breast tumors at an early stage of breast cancer or for the detection of breast cancer metastases. Two examples have been shown. A small tumor with a slow growth rate, expressing steroid receptor, was detectable with a labeled NTS analogue. This tumor generated over a long period of time with well differentiated cells indicates that this experimental approach allows the detection of tumors expressing NTSR1 at early stages of breast cancer. The larger tumor labeling and the staining of metastasis in the axillary area indicate the possible use of imagery using a NTS labeled analogues for the detection of distant metastatic sites.

In conclusion, based on a series of 106 patients with invasive ductal breast cancer, we provide evidence for NTS/NTSR1 as a contributor to breast cancer progression. Identification of breast cancer patients characterized by paracrine NTS/NTSR1 signaling pathway, as evidenced in the present study, provides alternative strategies to improve the treatment of IDCs. These findings support the therapeutic potential of NTS/NTSR1 inhibition or drug cellular targeting through NTSR1 in advanced stages of human breast cancers. Imaging experiments strongly advance the concept of using NTS analogues for early and late detection of human breast tumors and its metastatic site expressing NTSR1.

Patients and Methods

Breast Biopsies

Clinical file of 106 patients completely resected for invasive ductal breast cancers (IDCs) by tumorectomy or mastectomy, at the Gynecology Department, Hôtel-Dieu Hospital, Paris, were studied. Patients were diagnosed by the same oncologist for a period from June 1984 through May 1998. Clinico-pathological information was derived retrospectively from patient records. Survival and follow-up durations were measured as the time between the first histological confirmation of breast cancer and the last consultation in the department, or death. Patient records were reviewed retrospectively for demographical characteristics, clinical data, outcome, and survival. The histological diagnosis was routinely checked by microscopic examination of sections stained with hematoxylin-eosin.

Immunohistochemistry

Breast tumor sections of 5 μm thickness were analyzed by immunohistochemistry for NTSR1, NTS, ER, and PR staining, using the following antibodies: a NTSR1 goat polyclonal antibody (C-20 Santa Cruz USA), a NTS rabbit antibody (NA1230 Biomol, USA), a ER-α monoclonal antibody (Santa Cruz), a PR monoclonal antibody (Santa Cruz). Immunostaining was carried out on deparaffinized sections using the streptavidin biotin peroxidase complex method as described previously by Souaze et al (Souaze et al (2006) Cancer Res. 66:6243-6249). All slides were counterstained with hematoxylin. A semi-quantitative estimation of the number of positive cells was performed by counting 1 000 reactive and non-reactive cells in ten successive fields at the original 200× magnification.

Normal Breast Tissues

Normal human breast epithelial cells (HBEC) were cultured as previously described in Gompel et al. (Gompel et al. (1986) J. Clin. Endocrinol. Metab 63:1174-1180). Additional biopsies of normal breast tissues from 25 premenopausal women of various ages (18-50 years) undergoing plastic surgery were obtained according to the French regulations on clinical experimentation.

RNA Extraction and RT-PCR

The protocols for total RNA extraction, reverse-transcription reaction (RT), and PCR are documented in Souaze et al (Souaze F, Rostene W, Forgez P (1997) J. Biol. Chem. 272: 10087-10094). RT was performed on 1 μg of total RNA using a specific NTSR1 primer (5'-GCTGACGTAGAAGAG-3' SEQ ID NO:3) or 50 pmol of oligo dT and oligo dN. The PCR amplification was performed on a 1:5 v/v of the RT reaction using 25 pmol of each primer 5'-CGTGGAGCTGTA-CAACTTCA-3' SEQ ID NO:4 and 5'-CAGCCAGCAGAC-CACAAAGG-3' SEQ ID NO:5 for NTSR1, and 5'-AAGCA-CATGTTCCCTCTT-3' SEQ ID NO:6 and 5'-CATACAGCTGCCGTTTCAGA-3' SEQ ID NO:7 for NTS, and 1 unit of Taq polymerase (Applied Biosystems, Courtaboeuf, France). The amplification profile consisted of denaturation at 94° C. for 30 s, annealing at 57° C. for 45 s, and extension at 72° C. for 45 s. The PCR cycle were preceded by denaturation at 95° C. for 15 min and were followed by a final extension at 72° C. for 7 min.

Hormonal Treatments

HBEC were synchronized for 40 h in Ham F10 phenol red free medium containing 20 μM lovastatin. Synchronization was stopped by adding 2 mM mevalonate to the hormone-containing medium. Subsequently, cells were treated 48 h in a phenol red free medium containing 5% of compatible human serum with 10 nM estradiol (E2) with or without 1 μM ICI 182780.

NTS Expressing Cell Lines and Tumor Formation

MCF-7 cells were transfected by NTS coding sequence expressing vector. Stable clones were obtained using geneticin antibiotic selection. Two clones were chosen with differential NTS expression, NTS-h with high expression, and NTS-1 with low expression. 3 million cells with either MCF-7 or NTS-h were injected subcutaneously into the flank of nude mice. Only mice xenografted with NTS-h cells developed tumors over long periods, 9 months for the experiments presented here.

Imaging Scintigraphy

Scintigraphic imaging was performed, under pentobarbital anaesthesia after iv injection with DTPA($^{111}$In)-NTS-analogue (30-50 pmol, 11.1 MBq), using a dedicated small animal IMAGER-S/CT system (Biospace Measures) equipped with parallel collimators (matrix 128__128, 15% energy window centred on two peaks 171 and 245 KeV). Planar acquisition was performed from 0 to 60 min post-injection for the time point 1 h, and during 45 min for the other time points.

Statistics

Analyses were processed with StatView Version 5 (Abacus Concepts, Berkeley, Calif., USA). Descriptive statistics were performed for each variable; quantitative results are presented as mean±SD and qualitative results are presented as a distribution of a number of patients. To compare the two groups, $\chi^2$ test was used for qualitative variables and t test for quantitative variables. A p value <0.05 was accepted as significant. Survival analysis was performed by Kaplan-Meier method and comparison with Log-Rank test. For multivariate analysis, Cox model was performed using R statistical package associated with the death of patients. These data support the activation of neurotensinergic deleterious pathways in breast cancer progression.

REFERENCES

Throughout this application, various references describe the state of the art to which this invention pertains. The disclosures of these references are hereby incorporated by reference into the present disclosure.

The invention claimed is:

1. A method for treating breast cancer, comprising the step of administering an effective amount of an inhibitor of the neurotensin activation of the neurotensin receptor 1 (NTSR1) to a subject in need thereof,
wherein said inhibitor of neurotensin activation of the neurotensin receptor 1 is selected from the group consisting of an antibody against neurotensin or a fragment thereof which binds to neurotensin, an antibody against the neurotensin receptor 1 or a fragment thereof which binds to the neurotensin receptor 1; and
wherein the subject in need thereof is a subject with a stage III or IV breast cancer displaying NTSR1-expressing cells.

* * * * *